United States Patent
Smith

(10) Patent No.: US 9,226,774 B2
(45) Date of Patent: Jan. 5, 2016

(54) VISUAL OBTURATOR WITH TIP OPENINGS

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 517 days.

(21) Appl. No.: 12/944,235

(22) Filed: Nov. 11, 2010

(65) Prior Publication Data
US 2011/0152910 A1 Jun. 23, 2011

Related U.S. Application Data

(60) Provisional application No. 61/287,400, filed on Dec. 17, 2009.

(51) Int. Cl.
| | |
|---|---|
| A61B 17/34 | (2006.01) |
| A61B 1/313 | (2006.01) |
| A61B 19/00 | (2006.01) |
| A61B 17/00 | (2006.01) |

(52) U.S. Cl.
CPC ........... *A61B 17/3496* (2013.01); *A61B 1/3132* (2013.01); *A61B 17/34* (2013.01); *A61B 19/5212* (2013.01); *A61B 2017/00907* (2013.01)

(58) Field of Classification Search
CPC .............. A61B 17/34; A61B 17/3496; A61B 19/5212; A61B 1/3132; A61B 2017/00907
USPC .................. 606/185, 167, 182, 170; 604/264, 604/164.01, 506
See application file for complete search history.

(56) References Cited

U.S. PATENT DOCUMENTS

| | | |
|---|---|---|
| 1,882,213 A | 10/1932 | Donovan |
| 3,652,100 A | 3/1972 | Baturka |
| 3,760,810 A | 9/1973 | Hoorn |
| 4,535,773 A | 8/1985 | Yoon |
| 4,601,710 A | 7/1986 | Moll |
| 4,607,619 A | 8/1986 | Seike et al. |
| 4,654,030 A | 3/1987 | Moll et al. |
| 4,700,694 A | 10/1987 | Shishido |
| 4,705,023 A | 11/1987 | Arai |
| 4,802,487 A | 2/1989 | Martin et al. |
| 4,878,485 A | 11/1989 | Adair |
| 5,066,288 A | 11/1991 | Deniega et al. |
| 5,104,382 A | 4/1992 | Brinkerhoff et al. |
| 5,169,397 A | 12/1992 | Sakashita et al. |
| 5,215,526 A | 6/1993 | Deniega et al. |

(Continued)

FOREIGN PATENT DOCUMENTS

| | | |
|---|---|---|
| EP | 0 426 407 B1 | 5/1991 |
| EP | 0 604 197 | 6/1994 |

(Continued)

OTHER PUBLICATIONS

European Search Report for EP 06006907, date of completion Nov. 9, 2006.

(Continued)

*Primary Examiner* — Thomas McEvoy
*Assistant Examiner* — Julie A Szpira

(57) ABSTRACT

The present disclosure relates to an optical obturator that facilitates the visualization of tissue therethrough during use. The optical obturator disclosed herein includes a housing that is disposed at a proximal end thereof, an elongate member that extends distally from the housing, a distal end formed of a substantially opaque material with one or more openings formed therein, and a shield member.

18 Claims, 5 Drawing Sheets

(56) References Cited

U.S. PATENT DOCUMENTS

| | | | |
|---|---|---|---|
| 5,217,441 A | 6/1993 | Shichman | |
| 5,224,951 A | 7/1993 | Freitas | |
| 5,224,952 A | 7/1993 | Deniega et al. | |
| 5,226,890 A | 7/1993 | Ianniruberto et al. | |
| 5,226,891 A | 7/1993 | Bushatz et al. | |
| 5,232,440 A | 8/1993 | Wilk | |
| 5,248,298 A | 9/1993 | Bedi et al. | |
| 5,250,068 A | 10/1993 | Ideguchi et al. | |
| 5,263,937 A | 11/1993 | Shipp | |
| 5,271,380 A | 12/1993 | Riek et al. | |
| 5,275,583 A * | 1/1994 | Crainich | 604/264 |
| 5,279,597 A | 1/1994 | Dassa et al. | |
| 5,290,276 A | 3/1994 | Sewell | |
| 5,308,336 A | 5/1994 | Hart | |
| 5,314,417 A | 5/1994 | Stephens et al. | |
| 5,334,150 A | 8/1994 | Kaali | |
| 5,336,206 A | 8/1994 | Shichman | |
| 5,354,302 A | 10/1994 | Ko | |
| 5,364,372 A | 11/1994 | Danks et al. | |
| 5,366,445 A | 11/1994 | Haber et al. | |
| 5,370,640 A | 12/1994 | Kolff | |
| 5,372,588 A | 12/1994 | Farley et al. | |
| 5,376,076 A | 12/1994 | Kaali | |
| 5,380,291 A | 1/1995 | Kaali | |
| 5,380,302 A | 1/1995 | Orth | |
| 5,385,553 A | 1/1995 | Hart | |
| 5,385,572 A | 1/1995 | Nobles et al. | |
| 5,387,197 A | 2/1995 | Smith et al. | |
| 5,391,152 A | 2/1995 | Patterson | |
| 5,399,167 A | 3/1995 | Deniega | |
| 5,411,515 A | 5/1995 | Haber et al. | |
| 5,431,151 A | 7/1995 | Riek et al. | |
| 5,441,041 A | 8/1995 | Sauer et al. | |
| 5,445,142 A | 8/1995 | Hassler | |
| 5,467,762 A | 11/1995 | Sauer et al. | |
| 5,471,705 A | 12/1995 | Dao | |
| 5,478,317 A | 12/1995 | Yoon | |
| 5,487,745 A | 1/1996 | McKenzie | |
| 5,496,259 A | 3/1996 | Perkins | |
| 5,522,833 A | 6/1996 | Stephens et al. | |
| 5,533,977 A | 7/1996 | Metcalf et al. | |
| 5,534,009 A | 7/1996 | Lander | |
| 5,538,509 A | 7/1996 | Dunlap et al. | |
| 5,545,150 A | 8/1996 | Danks et al. | |
| 5,551,947 A | 9/1996 | Kaali | |
| 5,554,137 A | 9/1996 | Young et al. | |
| 5,554,167 A | 9/1996 | Young et al. | |
| 5,562,696 A | 10/1996 | Nobles et al. | |
| 5,569,160 A * | 10/1996 | Sauer et al. | 600/114 |
| 5,569,291 A | 10/1996 | Privitera et al. | |
| 5,569,292 A | 10/1996 | Scwemberger et al. | |
| 5,571,133 A | 11/1996 | Yoon | |
| 5,591,191 A | 1/1997 | Kieturakis | |
| 5,591,192 A | 1/1997 | Privitera et al. | |
| 5,601,559 A | 2/1997 | Melker et al. | |
| 5,607,440 A | 3/1997 | Danks et al. | |
| 5,609,562 A | 3/1997 | Kaali | |
| 5,609,604 A | 3/1997 | Schwemberger et al. | |
| 5,620,188 A | 4/1997 | McCurry et al. | |
| 5,624,459 A | 4/1997 | Kortenbach et al. | |
| 5,632,717 A | 5/1997 | Yoon | |
| 5,658,236 A | 8/1997 | Sauer et al. | |
| 5,658,306 A | 8/1997 | Kieturakis et al. | |
| 5,662,613 A | 9/1997 | Astarita | |
| 5,662,673 A | 9/1997 | Kieturakis | |
| 5,669,885 A | 9/1997 | Smith | |
| 5,674,184 A * | 10/1997 | Hassler, Jr. | 600/176 |
| 5,676,156 A | 10/1997 | Yoon | |
| 5,676,682 A | 10/1997 | Yoon | |
| 5,681,323 A | 10/1997 | Arick | |
| 5,685,820 A | 11/1997 | Riek et al. | |
| 5,690,663 A * | 11/1997 | Stephens | 606/185 |
| 5,690,664 A | 11/1997 | Sauer et al. | |
| 5,697,913 A | 12/1997 | Sierocuk et al. | |
| 5,709,671 A | 1/1998 | Stephens et al. | |
| 5,716,369 A | 2/1998 | Riza | |
| 5,720,761 A | 2/1998 | Kaali | |
| 5,738,628 A | 4/1998 | Sierocuk | |
| 5,772,660 A | 6/1998 | Young et al. | |
| 5,772,678 A | 6/1998 | Thomason et al. | |
| 5,776,112 A | 7/1998 | Stephens et al. | |
| 5,797,943 A | 8/1998 | Danks et al. | |
| 5,797,944 A | 8/1998 | Nobles et al. | |
| 5,807,317 A | 9/1998 | Krech, Jr. | |
| 5,807,338 A | 9/1998 | Smith et al. | |
| 5,817,061 A | 10/1998 | Goodwin et al. | |
| 5,827,315 A | 10/1998 | Yoon | |
| 5,843,039 A | 12/1998 | Klemm | |
| 5,843,115 A | 12/1998 | Morejon | |
| 5,857,999 A | 1/1999 | Quick et al. | |
| 5,860,996 A | 1/1999 | Urban et al. | |
| 5,868,773 A | 2/1999 | Danks et al. | |
| 5,873,889 A | 2/1999 | Chin | |
| 5,879,332 A | 3/1999 | Schwemberger et al. | |
| 5,893,369 A | 4/1999 | LeMole | |
| 5,904,699 A | 5/1999 | Schwemberger et al. | |
| 5,913,848 A | 6/1999 | Luther et al. | |
| 5,916,232 A * | 6/1999 | Hart | 606/185 |
| 5,947,930 A | 9/1999 | Schwemberger et al. | |
| 5,968,065 A * | 10/1999 | Chin | 606/190 |
| 5,971,958 A | 10/1999 | Zhang | |
| 5,980,493 A | 11/1999 | Smith et al. | |
| 5,980,549 A | 11/1999 | Chin | |
| 5,984,941 A | 11/1999 | Wilson et al. | |
| 5,997,510 A | 12/1999 | Schwemberger | |
| 6,007,481 A | 12/1999 | Riek et al. | |
| 6,017,356 A | 1/2000 | Frederick et al. | |
| 6,022,367 A | 2/2000 | Sherts | |
| 6,030,402 A | 2/2000 | Thompson et al. | |
| 6,036,657 A | 3/2000 | Milliman et al. | |
| 6,039,725 A | 3/2000 | Moenning et al. | |
| 6,063,099 A | 5/2000 | Danks et al. | |
| 6,099,544 A | 8/2000 | Wolf et al. | |
| 6,106,539 A | 8/2000 | Fortier | |
| 6,152,871 A | 11/2000 | Foley et al. | |
| 6,168,607 B1 | 1/2001 | Wattiez et al. | |
| 6,171,281 B1 | 1/2001 | Zhang | |
| 6,176,823 B1 | 1/2001 | Foley et al. | |
| 6,176,824 B1 | 1/2001 | Davis | |
| 6,203,557 B1 | 3/2001 | Chin | |
| 6,206,823 B1 | 3/2001 | Kolata et al. | |
| 6,209,886 B1 | 4/2001 | Estes et al. | |
| 6,228,058 B1 | 5/2001 | Dennis et al. | |
| 6,228,059 B1 | 5/2001 | Astarita | |
| 6,238,407 B1 | 5/2001 | Wolf et al. | |
| D443,360 S | 6/2001 | Haberland | |
| 6,245,011 B1 | 6/2001 | Dudda et al. | |
| 6,264,604 B1 | 7/2001 | Kieturakis et al. | |
| 6,282,442 B1 | 8/2001 | DeStefano et al. | |
| D449,887 S | 10/2001 | Haberland et al. | |
| 6,319,226 B1 | 11/2001 | Sherry | |
| 6,336,914 B1 | 1/2002 | Gillespie, III | |
| 6,364,840 B1 | 4/2002 | Crowley | |
| 6,478,806 B2 | 11/2002 | McFarlane | |
| 6,497,687 B1 | 12/2002 | Blanco | |
| 6,497,716 B1 | 12/2002 | Green et al. | |
| 6,544,277 B1 | 4/2003 | O'Heeron et al. | |
| 6,613,063 B1 | 9/2003 | Hunsberger | |
| 6,656,198 B2 | 12/2003 | Tsonton et al. | |
| 6,685,630 B2 | 2/2004 | Sauer et al. | |
| 6,695,816 B2 | 2/2004 | Cassidy | |
| 6,716,201 B2 * | 4/2004 | Blanco | 604/274 |
| 6,719,746 B2 | 4/2004 | Blanco | |
| 6,719,772 B2 | 4/2004 | Trask et al. | |
| 6,830,578 B2 | 12/2004 | O'Heeron et al. | |
| 6,835,201 B2 | 12/2004 | O'Heeron et al. | |
| 6,837,874 B1 | 1/2005 | Popov | |
| 6,884,253 B1 | 4/2005 | McFarlane | |
| 6,960,164 B2 | 11/2005 | O'Heeron | |
| 6,989,003 B2 | 1/2006 | Wing et al. | |
| D518,177 S | 3/2006 | Blanco | |
| D531,726 S | 11/2006 | Blanco et al. | |
| 7,320,694 B2 | 1/2008 | O'Heeron | |
| 7,344,519 B2 | 3/2008 | Wing et al. | |

(56) References Cited

U.S. PATENT DOCUMENTS

| | | |
|---|---|---|
| 7,758,603 B2 | 7/2010 | Taylor et al. |
| 7,824,327 B2 | 11/2010 | Smith |
| 2002/0026207 A1* | 2/2002 | Stellon et al. ............... 606/185 |
| 2002/0072713 A1 | 6/2002 | Almond et al. |
| 2002/0133188 A1 | 9/2002 | O'Heeron et al. |
| 2002/0143236 A1 | 10/2002 | Sauer |
| 2003/0100914 A1 | 5/2003 | O'Heeron et al. |
| 2003/0109894 A1 | 6/2003 | Blanco |
| 2004/0230155 A1 | 11/2004 | Blanco et al. |
| 2004/0230217 A1 | 11/2004 | O'Heeron |
| 2005/0038466 A1 | 2/2005 | O'Heeron et al. |
| 2005/0065543 A1* | 3/2005 | Kahle et al. ............... 606/190 |
| 2005/0107816 A1 | 5/2005 | Pingleton et al. |
| 2005/0119676 A1 | 6/2005 | Bumbalough et al. |
| 2005/0203559 A1 | 9/2005 | O'Heeron |
| 2005/0209623 A1 | 9/2005 | Patton |
| 2005/0251190 A1 | 11/2005 | McFarlane |
| 2005/0261717 A1 | 11/2005 | Sauer et al. |
| 2006/0030870 A1 | 2/2006 | Staudner |
| 2006/0149302 A1 | 7/2006 | Popov |
| 2006/0173479 A1* | 8/2006 | Smith ............... 606/185 |
| 2006/0200095 A1 | 9/2006 | Steube |
| 2006/0200182 A1 | 9/2006 | Prosek |
| 2007/0005087 A1 | 1/2007 | Smith et al. |
| 2007/0010842 A1 | 1/2007 | Popov |
| 2007/0016237 A1 | 1/2007 | Smith |
| 2007/0135679 A1 | 6/2007 | Hunt et al. |
| 2010/0063356 A1* | 3/2010 | Smith ............... 600/114 |

FOREIGN PATENT DOCUMENTS

| | | |
|---|---|---|
| EP | 0 684 016 | 11/1995 |
| EP | 0 815 796 | 1/1998 |
| EP | 1 994 897 | 11/2008 |
| EP | 2044896 A1 | 4/2009 |
| WO | WO 94-04082 | 3/1994 |
| WO | WO95/13751 | 5/1995 |
| WO | 03/026512 A1 | 4/2003 |
| WO | WO2004/002337 | 1/2004 |

OTHER PUBLICATIONS

Partial European Search Report for EP 06006907, date of completion Aug. 3, 2006.

European Search Report EP 08 25 3194 dated Feb. 17, 2009.

European Search Report for corresponding EP10252128 date of mailing is Jul. 6, 2011 (3 pages).

Australian Examination Report, Application No. 2010246402 dated Jan. 8, 2015.

European Examination Report dated Jul. 2, 2015, issued in European Application No. 10 252 128.

* cited by examiner

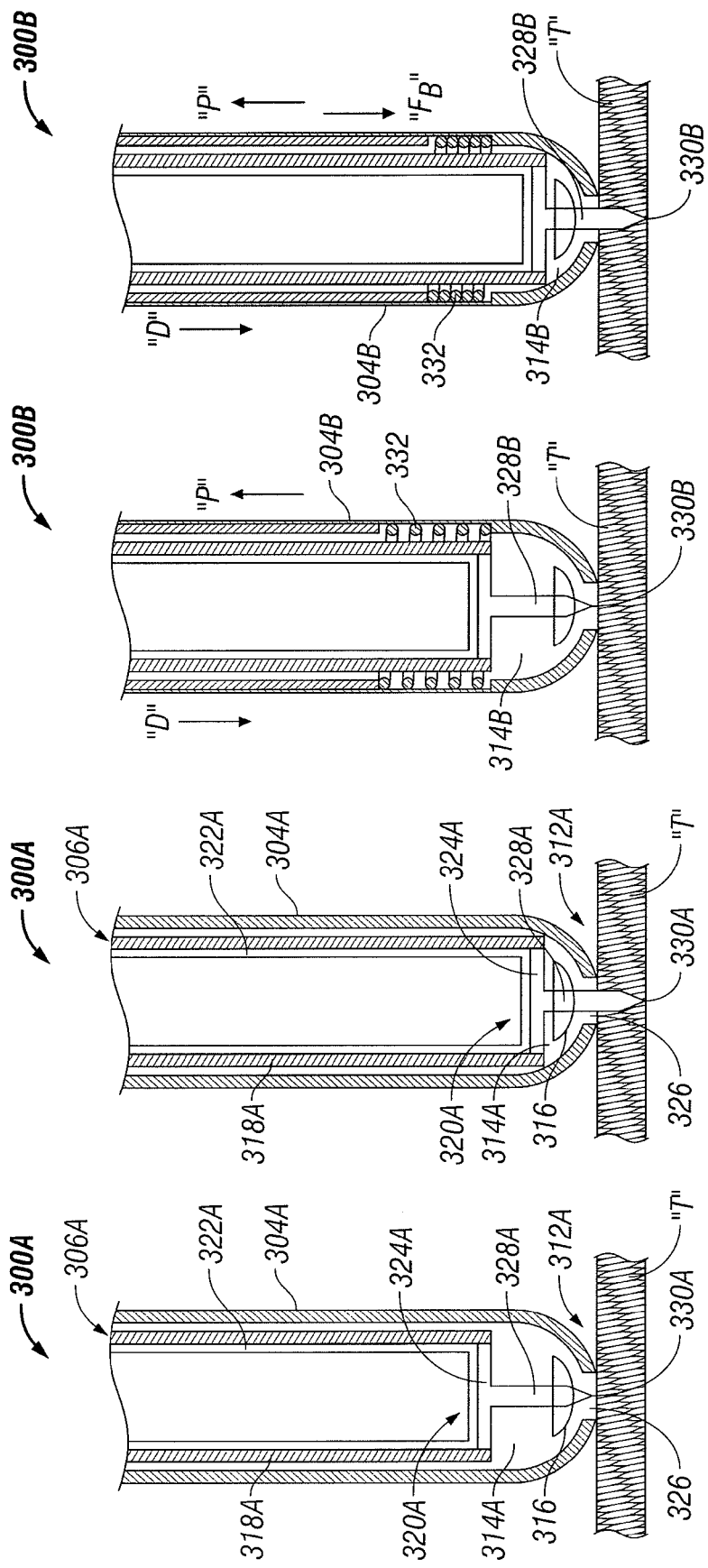

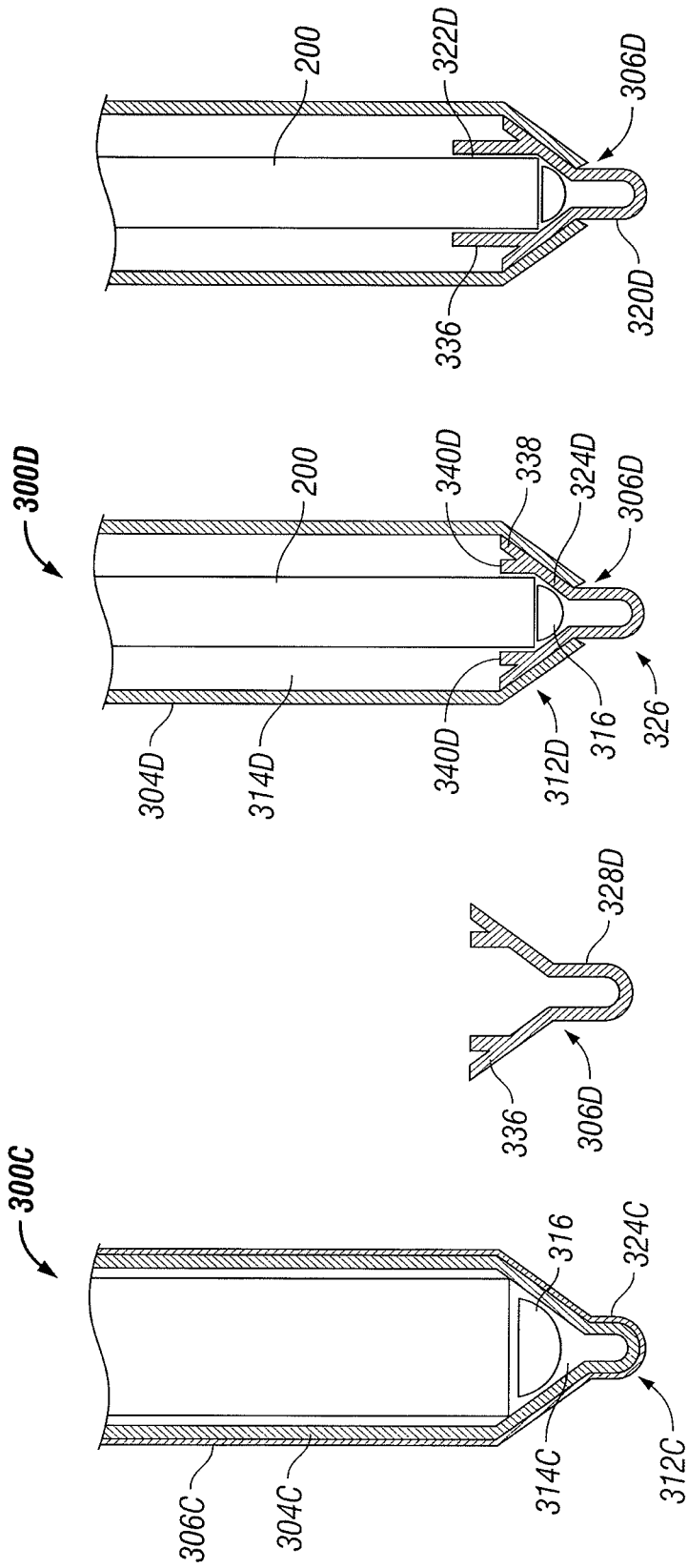

VISUAL OBTURATOR WITH TIP OPENINGS

CROSS REFERENCE TO RELATED APPLICATION

The present application claims the benefit of and priority to U.S. Provisional Application Ser. No. 61/287,400 filed on Dec. 17, 2009, the entire contents of which are incorporated herein by reference.

BACKGROUND

1. Technical Field

The present invention relates to an apparatus for the penetration of body tissue. More particularly, the present invention relates to an optical obturator having an opaque distal end that includes one or more openings to facilitate the viewing of tissue.

2. Background of Related Art

In endoscopic and laparoscopic procedures, surgery is performed in any hollow viscus of the body through narrow tubes or cannulas inserted percutaneously through a small incision or access point in the skin. Generally, in such procedures, the surgical region is first insufflated. Thereafter, a surgical access assembly, such as a cannula or trocar assembly, is typically used to create the incision or access point by advancing a surgical instrument through the skin. Such instruments may include an obturator, stylet, or trocar, and will collectively be referred to as obturators throughout the present disclosure. An example of a known obturator may be seen in commonly assigned U.S. Pat. No. 6,319,266 to Stellon, which issued Nov. 21, 2001, the contents of which are incorporated herein in its entirety by reference.

Endoscopic, and in particular, laparoscopic procedures, often require a clinician to act on organs, tissues or vessels that are far removed from the incision or access point that may be difficult to see, e.g. due to the location of the organ, tissue, or vessel, the presence of blood or other fluids, or the crowded nature of the surgical workspace. Consequently, many known surgical access assemblies are employed blindly. Accordingly, there exists a need in the art for an obturator which facilitates the viewing of the underlying workspace therethrough.

SUMMARY

The present disclosure relates to an optical obturator for use in accessing and penetrating body tissue during endoscopic procedures, laparoscopic procedures, and the like. The optical obturator includes an elongate member defining a first lumen therethrough and having proximal and distal ends. The distal end of the elongate member is formed of a substantially opaque material and includes at least one opening formed therein that is configured to facilitate the visualization of tissue. The optical obturator includes a shield member associated with the elongate member that is at least partially formed of an at least semi-transparent material, and may be configured for removable insertion within a surgical access assembly.

The present disclosure contemplates that the shield member may be disposed within the first lumen defined by the elongate member. In one embodiment, the shield member includes a second lumen that extends proximally from a distal end thereof that is configured to receive a visualization device. In this embodiment, the distal end of the elongate member includes an aperture that is configured to receive a penetrating element disposed at the distal end of the shield member, and the elongate member is repositionable between a plurality of positions, including a first position and at least one subsequent position.

In the first position, a distal-most tip of the penetrating element is concealed within the first lumen of the elongate member, and in the second position, the distal-most tip of penetrating element at least partially extends distally of the aperture. The obturator may further include a biasing member operatively associated with the elongate member to normally bias the elongate member toward the first position.

In another embodiment, the shield member is secured to an internal surface of the elongate member at the distal end thereof. The shield member may define a contoured portion that substantially approximates the configuration of the internal surface of the elongate member. It is contemplated that the shield member may exhibit a variety of profiles, one of which may be arcuate in configuration.

In yet another embodiment, the distal end of the elongate member includes a penetrating element and the shield member includes an optical member, e.g. a lens, disposed at a distal end thereof that is adapted to permit the passage of light therethrough.

In an alternate aspect of the present disclosure, the shield member is disposed externally of the obturator's elongate member, and may be so disposed in either a fixed or releasable manner.

In still another aspect of the present disclosure, the distal end of the elongate member is adapted to facilitate percutaneous entry through a patient's tissue. In alternate embodiments, the distal end of the elongate member of the obturator may be either substantially incisive or substantially blunt.

In a final embodiment, the distal end of the elongate member exhibits a profile that is at least partially tapered.

BRIEF DESCRIPTION OF THE DRAWINGS

The accompanying drawings, which are incorporated in, and constitute a part of this specification, illustrate embodiments of the disclosure and, together with a general description of the disclosure given above and the detailed description of the embodiment(s) given below, serve to explain the principles of the disclosure, wherein:

FIG. 4A is a side cross-sectional view of another embodiment of the optical obturator of FIG. 1 and the shield member of FIG. 2A shown in a first, or advanced position;

FIG. 4B is a side cross-sectional view of the optical obturator and shield member of FIG. 4A shown in a second, or retracted position;

FIG. 5A is a side cross-sectional view of one embodiment of the optical obturator and shield member of FIG. 4A shown in a first, or advanced position;

FIG. 5B is a side cross-sectional view of the optical obturator and shield member of FIG. 5A shown in a second, or retracted position;

FIG. 6 is a side cross-sectional view of another embodiment of the shield member of FIG. 2A disposed within the obturator of FIGS. 2A-2B;

FIG. 7A is a side view of another embodiment of the shield member of FIG. 2A;

FIG. 7B is a side cross-sectional view of the shield member of FIG. 7A disposed within the optical obturator of FIGS. 4A-4B;

FIG. 7C is a side cross-sectional view of another embodiment of the shield member of FIGS. 7A-7B disposed within the optical obturator of FIGS. 4A-4B.

DESCRIPTION OF EMBODIMENTS

Figure 1:
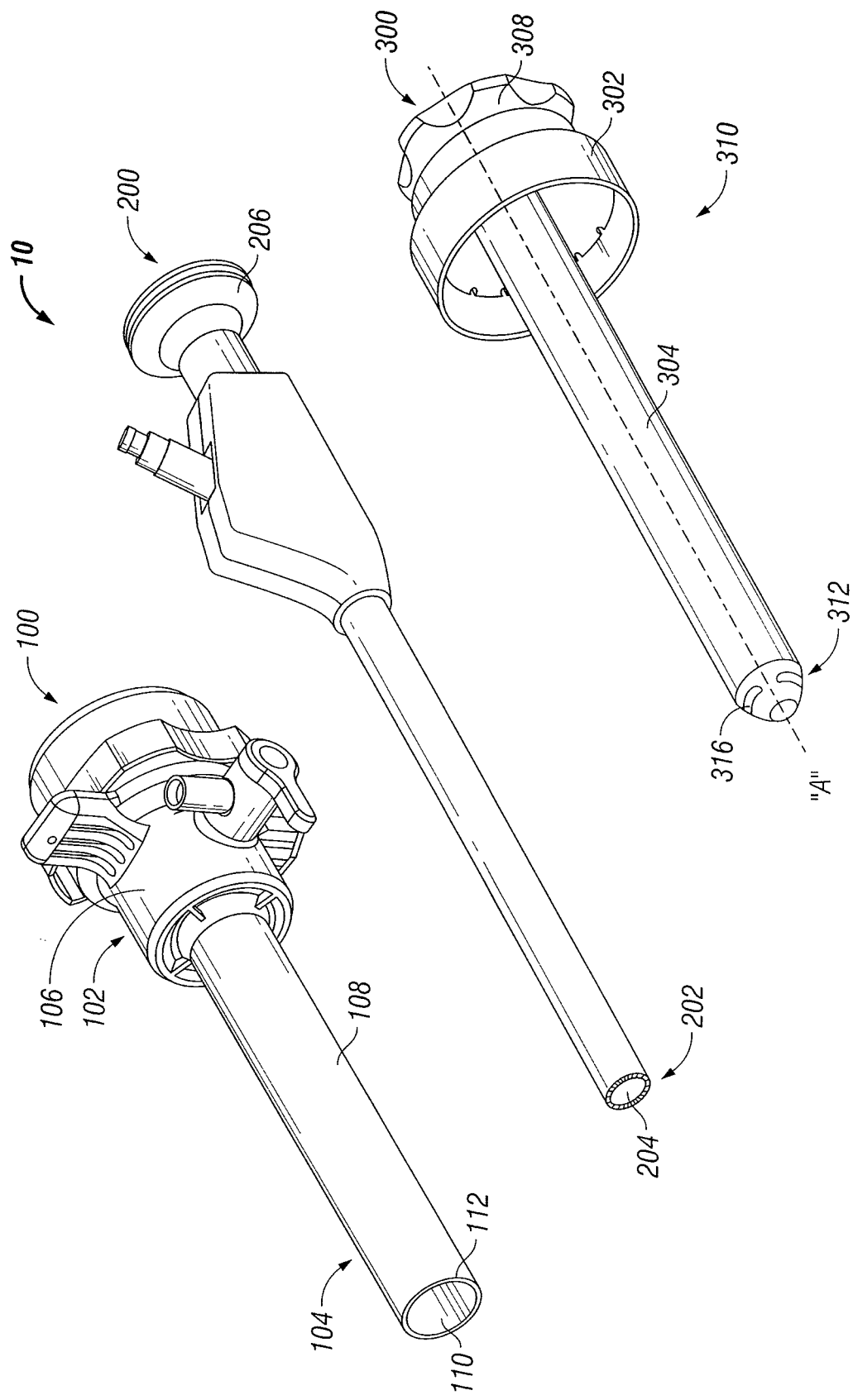
FIG. 1 is a perspective view of a surgical system in accordance with the principles of the present disclosure illustrating a surgical access assembly, a visualization device, and an optical obturator in accordance with the principles of the present disclosure.

Specific embodiments of the presently disclosed apparatus and method will now be described in detail with reference to the foregoing figures wherein like reference numerals identify similar or identical elements. In the figures, and in the description which follows, as is traditional, the term "proximal" will refer to the end of the apparatus or instrument of the present disclosure which is closest to the clinician, while the term "distal" will refer to the end of the device or instrument which is furthest from the clinician. In addition, throughout the present disclosure, the term "opaque" is to be interpreted as describing the ability of a material to substantially prevent the passage of visible light or other radiation utilized for imaging purposes therethrough, while the term "transparent" is to be interpreted as describing the ability of a material to substantially permit the passage of any such light or radiation therethrough, either with or without clear imaging capabilities. Moreover, the term "transparent" should be construed throughout this disclosure as inclusive of any material that is either transparent or translucent in nature, i.e. any material that is not opaque. Finally, the term "biocompatible material" shall be understood as any material possessing the quality of not having toxic or injurious effects on biological systems, including stainless steel, titanium, or any presently known or later devised alloy thereof, or alternatively, a polymeric material, such as polycarbonate, polystyrene, or the like.

Referring now to the drawings, FIG. 1 illustrates a surgical system 10 in accordance with the principles of the present disclosure. System 10 has particular application in endoscopic procedures, laparoscopic procedures, and the like, and includes a surgical access or portal assembly 100, a visualization device 200, and an optical obturator 300 that is the subject of the present disclosure.

Surgical access assembly 100 has a proximal end 102, a distal end 104, a valve or seal housing 106 disposed at a proximal end 102, and a shaft or elongate member 108 that extends distally from valve housing 106.

Valve housing 106 is configured for the removable insertion of a surgical instrument, e.g. optical obturator 300, and for the internal receipt of a surgical valve or seal member (not shown). Valve housing 106 may be any structure suitable for these intended purposes and may be formed of any suitable biocompatible material. Further information regarding valve housing 106 may be obtained through reference to commonly owned U.S. Pat. No. 7,169,130 to Exline et al., the entire contents of which are hereby incorporated by reference.

Extending distally from valve housing 106 is elongate member 108. Elongate member 108 defines a lumen 110 that extends longitudinally therethrough that is configured for the removable insertion of a surgical instrument, e.g. optical obturator 300, and may be formed of any suitable biocompatible material. At a distal end 104, elongate member 108 defines an opening 112 that is configured to allow the surgical instrument to pass therethrough.

Visualization device 200 may be any device suitable for the intended purpose of facilitating the visualization of tissue during the course of a surgical procedure. In one embodiment, visualization device 200 may be any conventional scope suitable for laparoscopic or endoscopic applications including, e.g., a laparoscope, endoscope, arthroscope, colonoscope, or the like. As an illustrative example, visualization device 200 may be the scope disclosed in commonly assigned U.S. Pat. No. 5,412,504 to Leiner (hereinafter "Leiner"), the entire contents of which are hereby incorporated by reference. Visualization device 200 is configured to transmit an image from a distal end 202, which includes a window 204, to an eye piece 206 for viewing by the clinician, and may incorporate an illuminating system (not shown) for providing light. Although depicted as incorporating an eyepiece 206 throughout the present disclosure, visualization device 200 may, either additionally or alternatively, be connected to a monitor or screen (not shown). Further details regarding visualization device 200 may be ascertained through reference to Leiner. Prior to the commencement of the surgical procedure, visualization device 200 may be at least partially positioned within optical obturator 300, as discussed in further detail below.

With reference now to FIGS. 1-8, the optical obturator 300 that is the subject of the present disclosure will be discussed. In each of the following embodiments, the proximal end of the device (not shown) is substantially similar to that of optical obturator 300, and will therefore not be discussed in the interests of brevity.

Figure 2A:
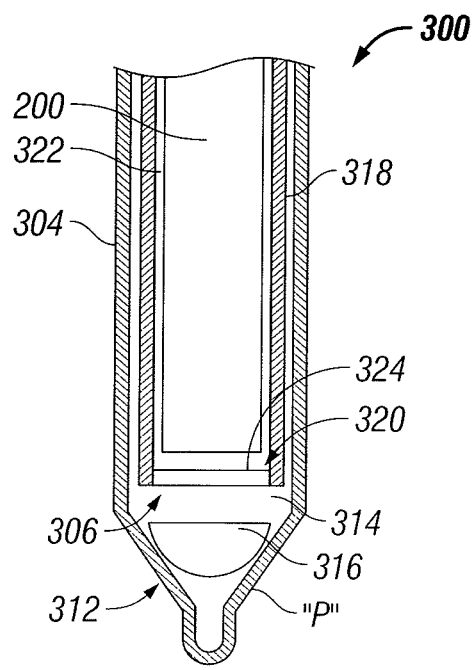
FIG. 2A is a side cross-sectional view of one embodiment of the optical obturator of FIG. 1 depicting a novel shield member.

FIGS. 1 and 2A depicts an exemplary optical obturator 300 that includes a housing 302, an elongate member 304 extending distally from housing 302 along a longitudinal axis "A", and a shield member 306 that is associated with elongate member 304.

Housing 302 may be advantageously dimensioned for grasping by the clinician, and may be formed from any suitable biocompatible material. In one embodiment, housing 302 includes a locking mechanism 308 or other structure suitable for the intended purpose of securing an instrument therein, such as visualization device 200 for example, as described in commonly assigned U.S. patent application Ser. No. 11/103,892 to Smith, the entire contents of which are hereby incorporated by reference.

Elongate member 304 has a proximal end 310, a distal end 312, and defines a longitudinal lumen 314 that extends at least partially therethrough that is configured for the removable insertion of visualization device 200. Elongate member 304 may be fabricated from any suitable biocompatible material.

In each of the embodiments disclosed herein, upon the insertion of visualization device 200 into elongate member 304 of optical obturator 300, visualization device 200 remains disposed proximally of a distal end 320 of shield member 306 throughout the course of the surgical procedure in which optical obturator 300 is employed, as discussed in further detail below.

Figure 2B:
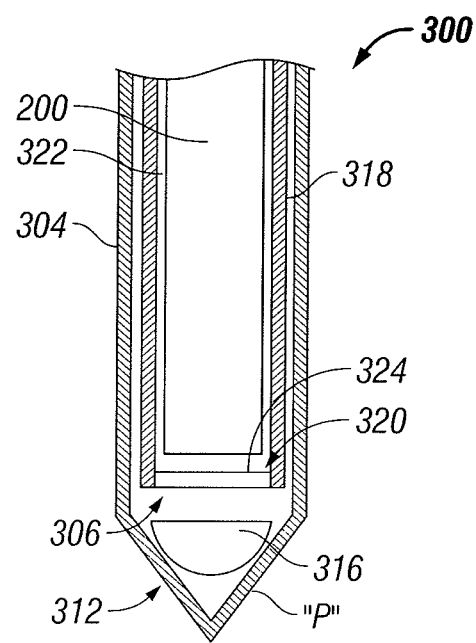
FIG. 2B is a side cross-sectional view of one another embodiment of the optical obturator of FIG. 1.

Distal end 312 of elongate member 304 is configured for percutaneous insertion into the tissue (not shown) of a patient and may be configured in any manner suitable for this intended purpose. Distal end 312 may be configured for insertion into a percutaneous opening, incision, or puncture that is pre-formed in the tissue, as depicted in FIG. 2A. In this embodiment, distal end 312 is configured to dilate the percutaneous opening upon the insertion of optical obturator 300 and exhibits a substantially blunt configuration. As seen in FIG. 2B, in an alternate embodiment, distal end 312 is configured to create the percutaneous opening, and to that end, is substantially incisive in configuration. In each of the embodiments of FIGS. 2A-2B, distal end 312 exhibits a substantially tapered profile "P" having a diameter that steadily decreases. However, an optical obturator 300 having a distal end 312 that exhibits a configuration with a substantially uniform diameter is also within the scope of the present disclosure. Distal end 312 includes outer wall 315 having one or more openings 316 formed therein that are configured to facilitate the visualization of tissue through optical obturator 300 by visualization device 200 upon the insertion of visualization device 200 into optical obturator 300. Openings 316 may exhibit any suitable configuration, including but not being limited to an elliptical, circular, or arcuate configuration.

As seen in FIGS. 2A-2B, shield member 306 is disposed within elongate member 304 of optical obturator 300 and includes an outer member 318 and a distal end 320. During the insertion of optical obturator 300 through tissue, and the subsequent distal advancement thereof, any tissue or bodily fluids that may enter lumen 314 through openings 316 formed in distal end 312 of optical obturator 300 will encounter shield member 306, and will therefore not obscure the images captured by visualization device 200.

Outer member 318 of shield member 306 defines a second lumen 322 that is configured to removably receive visualization device 200. Outer member 318 may be formed of any suitable biocompatible material that may be partially or wholly opaque or transparent.

Distal end 320 of shield member 306 includes a visualization portion 324 that is formed of an at least partially transparent material such that light may pass therethrough. This facilitates the visualization of tissue through visualization device 200 and optical obturator 300 by a clinician, as described in further detail below. In alternate embodiments, visualization portion 324 may comprise, either in whole or in part, a lens, and may be substantially flat or at least partially arcuate in configuration.

In alternate embodiments, the present disclosure contemplates that shield member 306 may be fixedly, movably, or releasably disposed within elongate member 304 of optical obturator 300. Additionally, although depicted as disposed within elongate member 304 in FIGS. 2A-2B, in alternate embodiments, shield member 306 may be associated with elongate member 304 in any suitable manner, including but not limited to being connected to, disposed within, or disposed externally of elongate member 304, as discussed below.

Referring now to FIGS. 4-8, various embodiments of optical obturator 300 and shield member 306 will be discussed. With reference to FIGS. 4A-4B in particular, optical obturator $300_A$ is disclosed. Optical obturator $300_A$ is substantially similar to the exemplary optical obturator 300 discussed above and seen in FIGS. 2-3, but for distal end $312_A$, which is discussed in further detail below, and includes elongate member $304_A$ that defines a first lumen $314_A$, and shield member $306_A$.

Distal end $312_A$ of optical obturator $300_A$ includes one or more openings 316 formed therein, as discussed above with respect to optical obturator 300, and defines an aperture 326 that is configured to receive a portion of shield member $306_A$, as discussed in further detail below.

Shield member $306_A$ is disposed within a lumen $314_A$ defined by elongate member $304_A$ of optical obturator $300_A$. Shield member $306_A$ includes an outer member $318_A$ and a distal end $320_A$.

Outer member $318_A$ of shield member $306_A$ defines a second lumen or cavity $322_A$ that is configured to removably receive visualization device 200. Outer member $318_A$ may be formed of any suitable biocompatible material that may be either partially or wholly opaque or transparent.

Distal end $320_A$ of shield member $306_A$ includes a penetrating element $328_A$, which includes a distal-most tip $330_A$, and a visualization portion $324_A$. Visualization portion $324_A$ is at least partially transparent such that light may pass therethrough, thereby facilitating the visualization of tissue by a clinician, as discussed above with respect to the embodiment of FIGS. 2-3. In one embodiment, visualization portion $324_A$ may comprise, either in whole or in part, a lens.

Penetrating element $328_A$ may be either substantially blunt or incisive dependent upon the particular surgical application in which optical obturator $300_A$ may be employed, and may be configured in any manner suitable for the intended purpose of facilitating percutaneous access to the internal cavities of a patient.

Shield member $306_A$ is engagable with elongate member $304_A$ of obturator $300_A$ such that elongate member $304_A$ is adapted for reciprocal longitudinal movement relative to the shield member $306_A$ between a plurality of conditions including a first, or advanced position (FIG. 4A), and at least one subsequent position, including a retracted, position (FIG. 4B). Any means of engagement between shield member $306_A$ and elongate member $304_A$ suitable for the intended purpose of facilitating the aforementioned reciprocal longitudinal movement is within the scope of the present disclosure. In the first position, penetrating element 328 is concealed within lumen $314_A$ of optical obturator $300_A$ such that distal-most tip $330_A$ of penetrating element $328_A$ does not extend distally beyond distal end $312_A$ of optical obturator $300_A$. In repositioning from the first position to the second position, elongate member $304_A$ moves proximally with respect to shield member $306_A$. As elongate member moves proximally, penetrating element $328_A$ is received by aperture 326 such that in the second position, distal-most tip $330_A$ extends distally beyond distal end $312_A$ of optical obturator $300_A$, thereby facilitating the creation of a percutaneous access site in tissue "T".

As seen in FIGS. 5A-5B, in one embodiment, optical obturator $300_B$ includes a biasing member 332, e.g. a spring, that is operatively associated with elongate member $304_B$. Biasing member 332 normally biases elongate member $304_B$ of obturator $300_B$ toward the first, or advanced position, such that distal-most tip $330_B$ of penetrating element $328_B$ of shield member $306_B$ is disposed within first lumen $314_B$ of optical obturator $300_B$ when optical obturator $300_B$ is not in use. As seen in FIG. 5B, upon the introduction of optical obturator $300_B$ to tissue "T", elongate member $304_B$ begins to retract or move proximally with respect to shield member $306_B$ in the direction indicated by arrow "P". As optical obturator $300_B$ is advanced distally, in the direction indicated by arrow "D", elongate member $304_B$ continues to move proximally, thereby facilitating contact between distal-most tip $330_B$ of penetrating element $328_B$, and the ultimate penetration of tissue "T".

During the distal advancement of optical obturator $300_B$, as elongate member $304_A$ moves proximally, biasing member 332 is contracted, thereby creating a biasing force "$F_B$" in biasing member 332. Biasing force "$F_B$" endeavors to expand biasing member 332 to its initial, pre-contraction length and thereby advance elongate member "$F_B$" distally, returning elongate member $304_B$ to the first position, due to the operative association of biasing member 332 with elongate member $304_B$. As optical obturator $300_B$ is withdrawn from tissue "T" in the direction of arrow "P", biasing force "$F_B$" acts on elongate member $304_B$, urging elongate member $304_B$ distally toward the first position such that upon complete removal of optical obturator $300_B$ from tissue "T", elongate member $304_B$ may be returned to the first position, thereby once again concealing penetrating element $328_B$ within first lumen $314_B$ of optical obturator $300_B$.

Referring now to FIG. 6, optical obturator $300_C$ is disclosed. Optical obturator $300_C$ is substantially similar to the optical obturator 300 disclosed in FIGS. 2-3 and discussed above, and includes an elongate member $304_C$ that defines a lumen $314_C$, and a shield member $306_C$.

Shield member $306_C$ is disposed externally of elongate member $304_C$ and is secured thereto in any suitable manner and at any suitable location proximal of distal end $312_C$ of optical obturator $300_C$. Shield member $306_C$ may be either fixedly secured to elongate member $304_C$, or shield member $306_C$ may be releasably secured thereto, such that shield member $306_C$ may be discarded after use.

In alternate embodiments, it is contemplated that shield member $306_C$ may be at least partially disposed within elongate member $304_C$ optical obturator 300. Shield member $306_C$ may be formed of any suitable biocompatible material, including but not being limited to stainless steel, titanium, or any presently known or later devised alloy thereof, or polymeric materials, such as polycarbonate, polystyrene, etc, and may be either substantially rigid or substantially flexible in character.

Shield member $306_C$ includes a visualization portion $324_C$ that is disposed about distal end $312_C$ of optical obturator 300. Visualization portion $324_C$ is at least partially transparent such that light may pass therethrough, as well as through openings 316 formed in distal end $312_C$ of optical obturator $300_C$, thereby facilitating the visualization of tissue, as discussed above with respect to each of the aforedescribed embodiments. The remaining portion of shield member $306_B$ may be formed, either wholly or in part, of a material that is either substantially opaque or substantially transparent.

As seen in FIGS. 7A-7B, in another embodiment, optical obturator $300_D$ is disclosed. Optical obturator $300_D$ is substantially similar to optical obturator $300_A$ discussed above and seen in FIGS. 4A-4B, and includes an elongate member $304_D$ that defines a lumen $314_D$, and a shield member $306_D$. Distal end $312_D$ of obturator $300_D$ includes one or more openings 316 formed therein, as discussed above with respect to each of the previously disclosed optical obturators.

Shield member $306_D$ is disposed within elongate member $304_D$ of obturator $300_D$ at a distal end $312_D$. Shield member $306_D$ includes a penetrating element $328_D$ and a connective member 336 having a visualization portion $324_D$. In alternate embodiments, shield member $306_D$ may be fixedly, movably, or releasably secured to elongate member $304_D$ of optical obturator $300_D$ in any suitable manner, including but not being limited to welding, through the use of adhesives, or through a snap-fit or interference arrangement.

Penetrating element $328_D$ is configured for receipt by aperture 326 formed in distal end $312_D$ of optical obturator $300_D$, as discussed above with respect to the optical obturator $300_A$ depicted in FIGS. 4A-4B. Penetrating element $328_D$ may be either substantially blunt or incisive dependent upon the particular surgical application in which obturator $300_D$ may be employed, and may be configured in any manner suitable for the intended purpose of facilitating percutaneous access to the internal cavities of a patient.

Connective member 336 extends proximally from penetrating element $328_D$ of shield member $306_D$ and constitutes the point of engagement between shield member $306_D$ and elongate member $304_D$ of optical obturator $300_D$. In one aspect of shield member $306_D$, as seen in FIG. 7A-7B, connective member 336 includes a contoured portion 338 that substantially approximates the configuration of penetrating element 334 of elongate member $304_D$ such that a substantially fluid tight seal is created between shield member $306_D$ and penetrating element 334 of elongate member $304_D$. In this embodiment, connective member $336_D$ is configured to engage visualization device 200 upon the insertion thereof into optical obturator $300_D$, and to that end, connective member $336_D$ includes an abutment portion $340_D$ defining dimensions that substantially approximate those of visualization device 200 such that visualization device 200 may be releasably received by abutment portion $340_D$. In an alternate embodiment, as seen in FIG. 7C, connective member 336 extends proximally from distal end $320_D$ of shield member $306_D$ such that a second lumen $322_D$ is defined that is configured to removably receive visualization device 200, as with the embodiments of FIGS. 2-4B.

Connective member 336 of shield member $306_D$ includes a visualization portion 324, which is formed of an at least partially transparent material such that light may pass therethrough and enter openings 316 formed in distal end $312_D$ of optical obturator $300_D$, thereby facilitating the visualization of tissue by a clinician using visualization device 200, as discussed above with respect to each of the previous embodiments. Whereas visualization portion $324_D$ is formed of an at least partially transparent material, the remaining portion of shield member $306_D$ may be formed of a material that is either substantially transparent or substantially opaque. In an alternate embodiment of shield member $306_D$, it is contemplated that connective member 336 may be entirely formed of an at least partially transparent material.

Figure 8:
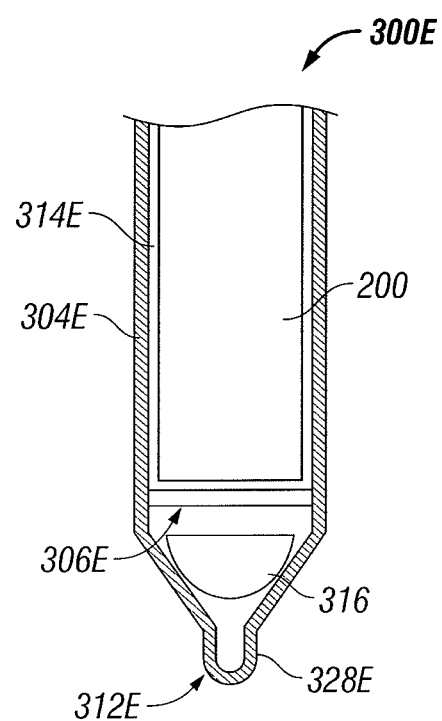
FIG. 8 is a side cross-sectional view of another embodiment of the shield member of FIG. 2A disposed within the optical obturator of FIGS. 2A-2B and FIG. 6.

Referring now to FIG. 8, in a further embodiment, optical obturator $300_E$ is disclosed. Optical obturator $300_E$ is substantially similar to optical obturators 300, $300_C$ discussed above and seen in FIGS. 2-3 and FIG. 6, respectively, and includes an elongate member $304_E$ that defines a lumen $314_E$, a distal end $312_E$ having a penetrating member $328_E$ and one or more openings 316 formed therein, and shield member $306_E$.

Shield member $306_E$ is disposed within lumen $314_E$ and may be releasably, fixedly, or movably secured to elongate member $304_E$ in any suitable manner. Shield member $306_E$ may be formed of any suitable biocompatible material that is at least partially formed of a transparent material such that light may pass therethrough and into visualization device 200 through openings 316 formed in distal end $312_E$ optical obturator $300_E$, thereby facilitating the visualization of tissue through optical obturator $300_E$, as discussed above with respect to each of the preceding embodiments. Shield member $306_E$ may include an abutment portion (not shown) that defines dimensions that substantially approximate those of visualization device 200 such that visualization device 200 may be releasably received by the abutment portion (not shown), as discussed above with respect to the embodiment of FIGS. 7A-7B.

Figure 3:
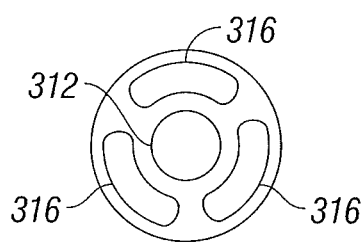
FIG. 3 is a bottom view of a distal end of the optical obturator of FIGS. 1-2.

Referring to FIGS. 1-3, the use and function of the system 10 will now be discussed. Throughout the following discussion, optical obturator 300 will be referred to in an illustrative capacity only and it should be understood that each of the embodiments of the optical obturator 300 and shield member 306 disclosed herein may be employed in a substantially similar manner.

Initially, the peritoneal cavity is first insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Following insufflation, visualization device 200 is positioned within optical obturator 300, specifically, within lumen 314 defined by elongate member 304. Visualization device 200 is advanced distally such that visualization device 200 is disposed substantially adjacent visualization portion 324 of shield member 306. Thereafter, visualization device 200 and optical obturator 300 are positioned within surgical access assembly 100. Optical obturator 300 is advanced distally until contact is made with tissue "T", at which time, penetrating element 328 facilitates the percutaneous insertion of optical obturator 300, and consequently, surgical access assembly 100. During the distal advancement of surgical access assembly 100 and optical obturator 300 through tissue "T", any tissue or bodily fluids that may enter lumen 314 of optical obturator 300 will encounter shield member 306, and will therefore not obscure the images captured by visualization device 200 through direct contact therewith.

While the above is a complete description of the embodiments of the present disclosure, various alternatives, modifications and equivalents may be used. Therefore, the above description should not be construed as limiting, but rather as illustrative of the principles of the disclosure made herein. Those skilled in the art will envision other modifications within the scope and spirit of the claims appended hereto.

What is claimed is:

1. An optical obturator, which comprises:
   an elongate member defining a longitudinal axis and having a first longitudinal lumen therethrough, the elongate member having proximal and distal ends and defining a generally tapered penetrating segment adjacent the distal end, the penetrating segment dimensioned to facilitate passage of the elongate member through tissue and having an outer wall segment with at least two openings extending through the outer wall segment in communication with the first longitudinal lumen; and
   a shield member at least partially disposed within the first longitudinal lumen of the elongate member, the shield member including an outer member defining a second longitudinal lumen dimensioned and configured for reception of a visualization device, the outer member having a closed distal window to prevent ingress of fluids within the second longitudinal lumen, the closed distal window being at least partially formed of an at least semi-transparent material to permit visualization with the visualization device at least through the at least two openings in the penetrating segment of the elongate member, the distal end of the shield member including a penetrating element extending from the closed distal window, the penetrating element dimensioned and adapted to penetrate tissue; and
   the elongate member being repositionable relative to the shield member between a first position, in which the penetrating element of the shield member is concealed within the first lumen of the elongate member, and at least one subsequent position, in which the penetrating element at least partially extends through and distally beyond one of the at least two openings extending through the outer wall segment of the penetrating segment of the elongate member.

2. The optical obturator according to claim 1, including a biasing member operatively associated with the elongate member to normally bias the elongate member toward the first position.

3. The optical obturator according to claim 1, wherein the closed distal window of the shield member includes a lens.

4. The optical obturator according to claim 1, wherein the penetrating segment of the elongate member is adapted to facilitate percutaneous entry into a subject.

5. The optical obturator according to claim 1, wherein the penetrating segment of the elongate member is substantially incisive.

6. The optical obturator according to claim 1, wherein the penetrating segment of the elongate member is substantially blunt.

7. The optical obturator according to claim 1, including a visualization device positionable within the second longitudinal lumen of the shield member.

8. The optical obturator according to claim 7, including a cannula defining a longitudinal axis and having a longitudinal passageway therethrough, the cannula dimensioned for passage through tissue, the elongate member being positionable within the longitudinal passageway of the cannula.

9. The optical obturator according to claim 1, wherein the at least two openings in the penetrating segment include a first opening in general alignment with the longitudinal axis of the elongate member.

10. The optical obturator according to claim 9, wherein the at least two openings include second and third openings which are displaced radially with respect to the longitudinal axis.

11. An optical apparatus, which comprises:
    a cannula defining a longitudinal axis and having a longitudinal passageway therethrough, the cannula dimensioned for passage through tissue;
    an obturator member positionable within the longitudinal passageway of the cannula, the obturator member including:
       an elongate member defining a longitudinal axis and having a first longitudinal lumen therethrough, the elongate member having proximal and distal ends and defining a generally tapered penetrating segment adjacent the distal end, the penetrating segment dimensioned to facilitate passage of the elongate member through tissue and having an outer wall segment with first and second openings extending through the outer wall segment in communication with the first longitudinal lumen;
       a shield member positioned within the first longitudinal lumen of the elongate member, the shield member including an outer member defining a second longitudinal lumen, the outer member having a closed distal window to prevent ingress of fluids within the second longitudinal lumen, the closed distal window comprising at least semi-transparent material, the closed distal window having a penetrating element, the shield member and the elongate member being adapted for relative longitudinal movement between a first relative position corresponding to a confined condition of the penetrating element within the elongate member and a second relative position corresponding to an extended condition of the penetrating element where the penetrating element extends at least partially through and beyond the first opening defined within the outer wall segment of the penetrating segment of the elongate member to facilitate advancement through tissue; and
    a visualization device positionable within the second longitudinal lumen of the shield member to enable visualization of tissue through the closed distal window and at least one of the first and second openings in the penetrating segment of the elongate member.

12. The optical apparatus according to claim 11, including a biasing member dimensioned to normally bias at least one of the elongate member or the shield member toward the first relative position.

13. The optical apparatus according to claim 11, wherein the closed distal window of the shield member includes a lens.

14. The optical apparatus according to claim 11, wherein the penetrating segment of the elongate member is adapted to facilitate percutaneous entry into a subject.

15. The optical apparatus according to claim 11, wherein the penetrating segment of the elongate member is substantially incisive.

16. The optical apparatus according to claim 11, wherein the penetrating segment of the elongate member is substantially blunt.

17. The optical apparatus according to claim 11, wherein the first opening in the outer wall segment of the penetrating segment is in general alignment with the longitudinal axis of the elongate member.

18. The optical apparatus according to claim 17, wherein the second opening in the outer wall segment of the penetrating segment is radially displaced with respect to the longitudinal axis.

* * * * *